(12) United States Patent  
Church

(10) Patent No.: US 10,737,464 B2  
(45) Date of Patent: Aug. 11, 2020

(54) STRUCTURE ADAPTED TO TRAVERSE A FLUID ENVIRONMENT AND METHOD OF RETROFITTING STRUCTURE ADAPTED TO TRAVERSE A FLUID ENVIRONMENT

(71) Applicant: Ryan Church, Toronto (CA)

(72) Inventor: Ryan Church, Toronto (CA)

(73) Assignee: BIOMERENEWABLES INC., Toronto (CA)

( * ) Notice: Subject to any disclaimer, the term of this patent is extended or adjusted under 35 U.S.C. 154(b) by 218 days.

(21) Appl. No.: 15/553,103

(22) PCT Filed: Feb. 25, 2016

(86) PCT No.: PCT/CA2016/050195  
§ 371 (c)(1),  
(2) Date: Aug. 23, 2017

(87) PCT Pub. No.: WO2016/134475  
PCT Pub. Date: Sep. 1, 2016

(65) Prior Publication Data  
US 2018/0045176 A1 Feb. 15, 2018

Related U.S. Application Data

(60) Provisional application No. 62/120,409, filed on Feb. 25, 2015.

(51) Int. Cl.  
*F03D 1/06* (2006.01)  
*B32B 9/02* (2006.01)  
(Continued)

(52) U.S. Cl.  
CPC .................. *B32B 9/02* (2013.01); *B64C 3/00* (2013.01); *C12N 1/16* (2013.01); *C12N 9/80* (2013.01);  
(Continued)

(58) Field of Classification Search  
CPC ...... F03D 1/065; F03D 1/0675; F03D 1/0683; F03D 1/0641; F03D 80/40; B64C 3/30;  
(Continued)

(56) References Cited

U.S. PATENT DOCUMENTS 6,015,115 A   1/2000   Dorsett et al.  
6,082,667 A *  7/2000   Haggard .................. B64C 9/02  
                                                    244/123.11

(Continued)

FOREIGN PATENT DOCUMENTS

EP     2159560     3/2010  
EP     2253834     11/2010  
(Continued)

OTHER PUBLICATIONS

Supplemental European Search Report issued in European Application No. EP 1 675 4707, dated Sep. 26, 2018.

*Primary Examiner* — Ninh H. Nguyen  
*Assistant Examiner* — Behnoush Haghighian  
(74) *Attorney, Agent, or Firm* — Norton Rose Fulbright Canada LLP

(57) ABSTRACT

A structure adapted to traverse a fluid environment exerting an ambient fluid pressure is provided. The structure includes an elongate body extending from a root to a wingtip and encapsulating at least one interior volume containing an interior fluid exerting an interior fluid pressure that is different from the ambient fluid pressure. A method of retrofitting a structure adapted to traverse a fluid environment exerting an ambient fluid pressure, the structure comprising an elongate body extending from a root to a wingtip and having at least one interior volume is also provided. The method includes sealing the elongate body to encapsulate the at least one interior volume containing an interior fluid; associating at least one valve with the at least one interior volume; and modifying interior fluid content via the at least (Continued)

one valve to produce an interior fluid pressure that is different from the ambient fluid pressure.

20 Claims, 3 Drawing Sheets

(51) Int. Cl.
| | |
|---|---|
| *C12N 11/00* | (2006.01) |
| *F03D 13/10* | (2016.01) |
| *B64C 3/00* | (2006.01) |
| *F01D 5/14* | (2006.01) |
| *F01D 21/00* | (2006.01) |
| *C12N 1/16* | (2006.01) |
| *C12N 9/80* | (2006.01) |
| *B64C 3/46* | (2006.01) |
| *B64C 3/30* | (2006.01) |
| *B64D 15/16* | (2006.01) |
| *F03D 80/40* | (2016.01) |
| *B33Y 70/00* | (2020.01) |
| *B33Y 10/00* | (2015.01) |
| *C12P 1/00* | (2006.01) |

(52) U.S. Cl.
CPC .............. *C12N 11/00* (2013.01); *F01D 5/147* (2013.01); *F01D 21/003* (2013.01); *F03D 1/065* (2013.01); *F03D 1/0675* (2013.01); *F03D 13/10* (2016.05); *B33Y 10/00* (2014.12); *B33Y 70/00* (2014.12); *B64C 3/30* (2013.01); *B64C 3/46* (2013.01); *B64D 15/166* (2013.01); *C12P 1/00* (2013.01); *F03D 1/0641* (2013.01); *F03D 1/0683* (2013.01); *F03D 80/40* (2016.05); *F05B 2230/30* (2013.01); *F05B 2230/50* (2013.01); *F05B 2230/80* (2013.01); *F05B 2240/21* (2013.01); *F05B 2240/57* (2013.01); *F05B 2270/107* (2013.01); *F05B 2270/17* (2013.01); *F05B 2270/301* (2013.01); *Y02B 10/30* (2013.01); *Y02E 10/721* (2013.01); *Y02P 70/523* (2015.11)

(58) Field of Classification Search
CPC ......... B64C 3/46; B64C 15/166; B64C 15/20; B64C 15/22
See application file for complete search history.

(56) References Cited

U.S. PATENT DOCUMENTS

| | | | |
|---|---|---|---|
| 7,708,229 B1 | 5/2010 | Angle, II | |
| 7,901,189 B2* | 3/2011 | Gupta | F03D 1/0675 416/230 |
| 7,938,623 B2* | 5/2011 | Cairo | F03D 1/065 416/226 |
| 8,753,091 B1* | 6/2014 | Braley | F03D 1/0675 416/226 |
| 2003/0122037 A1* | 7/2003 | Hyde | B64D 15/166 244/134 A |
| 2007/0110584 A1* | 5/2007 | Stommel | F03D 1/0675 416/233 |
| 2007/0189903 A1 | 8/2007 | Eyb | |
| 2009/0129925 A1 | 5/2009 | Vronsky et al. | |
| 2009/0224108 A1* | 9/2009 | Lutke | B64C 3/46 244/219 |
| 2009/0232635 A1 | 9/2009 | Menke | |
| 2009/0277266 A1 | 11/2009 | Wang | |
| 2010/0158688 A1* | 6/2010 | Benito | F03D 80/40 416/39 |
| 2011/0018268 A1* | 1/2011 | Snel | F03D 7/022 290/44 |
| 2011/0116927 A1* | 5/2011 | Hancock | F03D 1/0675 416/23 |
| 2012/0020803 A1* | 1/2012 | Lees | F03D 7/0236 416/233 |
| 2013/0022463 A1* | 1/2013 | Zuteck | F03D 7/022 416/1 |
| 2013/0235897 A1* | 9/2013 | Bouteyre | F03D 1/065 374/4 |

FOREIGN PATENT DOCUMENTS

| | | |
|---|---|---|
| GB | 2481415 | 12/2011 |
| WO | 2008132235 | 11/2008 |

* cited by examiner

STRUCTURE ADAPTED TO TRAVERSE A FLUID ENVIRONMENT AND METHOD OF RETROFITTING STRUCTURE ADAPTED TO TRAVERSE A FLUID ENVIRONMENT

CROSS-REFERENCE TO RELATED APPLICATION

This application claims priority under 35 U.S.C. 119(e) from U.S. Provisional Patent Application Ser. No. 62/120,409 entitled "METHOD OF MANUFACTURING AND MAINTAINING WIND TURBINE COMPONENTS" filed on Feb. 25, 2015, the contents of which are incorporated in their entirety herein by reference.

FIELD OF THE INVENTION

The following relates generally to structures adapted to traverse fluid environments, and more particularly to a structure adapted to traverse a fluid environment having an encapsulated fluid and a method for retrofitting.

BACKGROUND OF THE INVENTION

Horizontal-axis wind turbines for generating electricity from rotational motion are generally comprised of one or more rotor blades each having an aerodynamic body extending outwards from a horizontal shaft that is supported by, and rotates within, a wind turbine nacelle. The nacelle is supported on a tower which extends from the ground or other surface. Wind incident on the rotor blades applies pressure causing the rotor blades to move by rotating the shaft from which they extend about the horizontal rotational axis of the shaft. The shaft is, in turn, associated with an electricity generator which, as is well-known, converts the rotational motion of the shaft into electrical current for transmission, storage and/or immediate use. Horizontal-axis wind turbines are generally very well-known and understood, though improvements in their operation to improve the efficiency of power conversion and their overall operational characteristics are desirable.

Incident wind at even low speeds can cause the rotor blades to rotate quickly. As would be well-understood, for a given rotational velocity, the linear velocity of a rotor blade is lowest in the region of its root—the portion of the rotor blade proximate to the shaft. Similarly, the linear velocity of the rotor blade is highest in the region of its wingtip—the portion of the rotor blade distal from the shaft.

Wind turbines are increasing in popularity in recent years as a means of generating renewable energy. With this growth, there is increasing interest in turbine components that are efficient to maintain in good working condition and in methods of efficiently manufacturing components for the wind turbines and optimal locations for their operation have been subsequently declining, with these locations being limited.

It is known that current wind turbine blades are exposed to cyclical gravitational loading and edgewise loading during rotation, also known in the industry as 'breathing', where the blade expands and contracts. The expansions and contractions place stress on the bonding seams of rotor blades at the leading and trailing edge, as well as along spar cap and shear webs of the rotor blades. Through this continued stress, trailing edge, leading edge and transverse longitudinal cracks form, leading to eventually delamination and failures. The failures are thought to be a result of the Brazier effect, where over time the breathing causes steadily increasing curvature in the bonding seam areas leading eventually to a threshold curvature after which the object being curved becomes unstable and forms somewhat of a kink.

Various proposals for addressing the stresses placed on rotor blades have been made.

For example, PCT International Patent Application No. PCT/DK2009/000149 to Jensen, entitled "A REINFORCED WIND TURBINE BLADE" discloses an elongated reinforcing member connected to the shell of a wind turbine blade to improve the resistivity to compression forces experienced by the blade.

United States Patent Application Publication No. 2007/0189903 to Eyb, entitled "WIND TURBINE ROTOR BLADE" discloses a carbon fibre reinforced spar cap.

United States Patent Application Publication No. 2009/0129925 to Vronsky et al. entitled "WIND TURBINE BLADE LOAD SENSOR" discloses a wind turbine rotor blade root load sensor configured to be internally mounted within an insert of a root portion of a wind turbine rotor. The sensor is positioned along the internal wall of the root of a rotor blade, and detects torque and other bending forces.

United States Patent Application Publication No. 2009/0277266 to Wang entitled "METHODS AND APPARATUS FOR SENSING PARAMETERS OF ROTATING BLADES" discloses a method for monitoring operating parameters of a rotating blade having at least one sensor thereon, the sensor operatively coupled to a data acquisition device, where the data relates to blade acceleration measurements.

United States Patent Application Publication No. 2009/0232635 to Menke entitled "INDEPENDENT SENSING SYSTEM FOR WIND TURBINES" discloses a wireless sensing device for use in a wind turbine measuring multiple parameters and having an independent power source.

SUMMARY OF THE INVENTION

According to an aspect, there is provided a structure adapted to traverse a fluid environment exerting an ambient fluid pressure, the structure comprising an elongate body extending from a root to a wingtip and encapsulating at least one interior volume containing an interior fluid exerting an interior fluid pressure that is different from the ambient fluid pressure.

In an embodiment, the elongate body is a rotor blade for a wind turbine.

According to another aspect, there is provided a method of retrofitting a structure adapted to traverse a fluid environment exerting an ambient fluid pressure, the structure comprising an elongate body extending from a root to a wingtip and having at least one interior volume, the method comprising sealing the elongate body to encapsulate the at least one interior volume containing an interior fluid; associating at least one valve with the at least one interior volume; and modifying interior fluid content via the at least one valve to produce an interior fluid pressure that is different from the ambient fluid pressure.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures wherein.

DETAILED DESCRIPTION

Reference will now be made in detail to the various embodiments of the invention, one or more examples of which are illustrated in the figures. Each example is provided by way of explanation of the invention, and is not meant as a limitation of the invention. For example, features illustrated or described as part of one embodiment can be used on or in conjunction with other embodiments to yield yet a further embodiment. It is intended that the present invention includes such modifications and variations.

The present patent application includes description of opportunities for improving on the traditional aspects of a blade configuration for a wind turbine.

Figure 1:
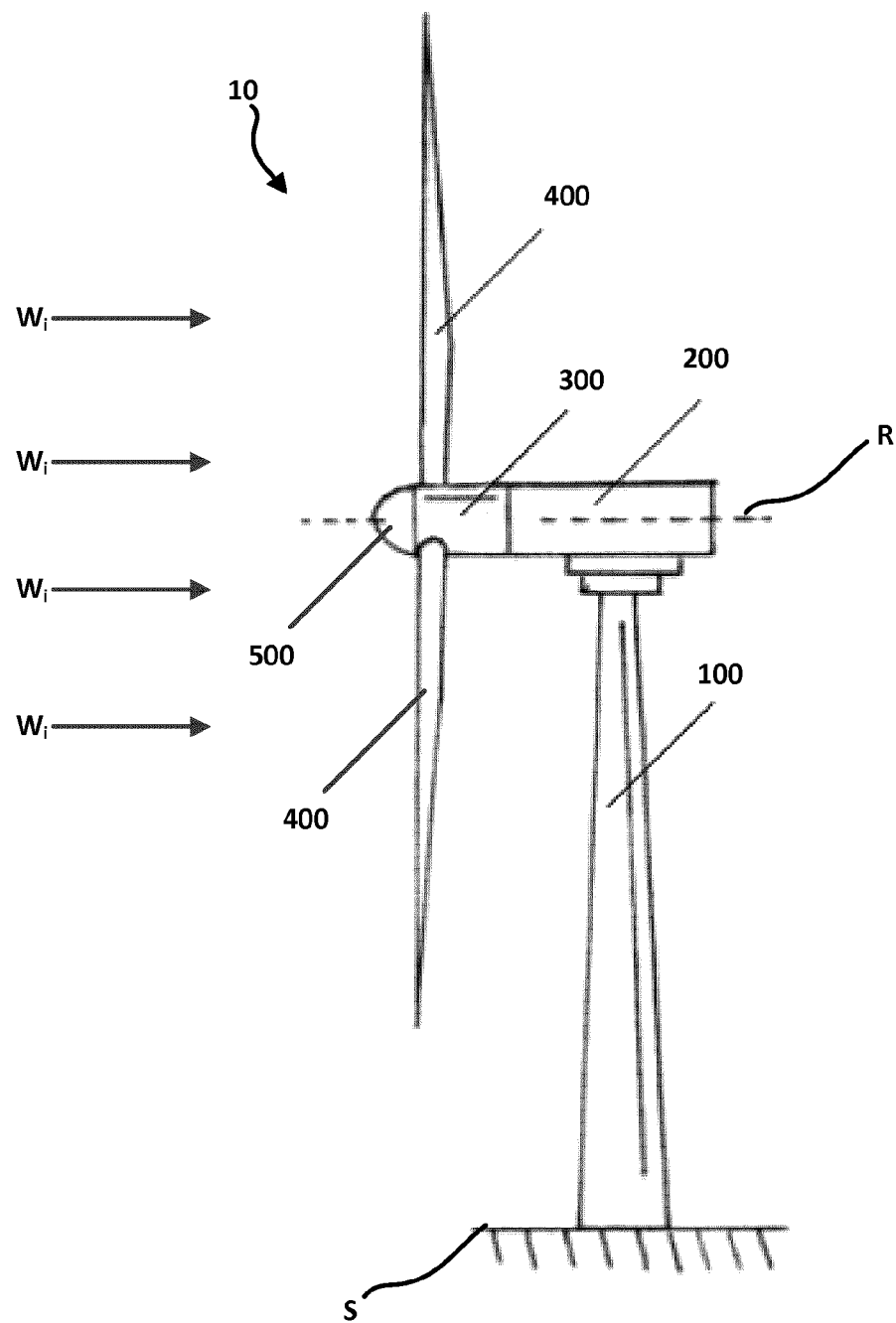
FIG. 1 is a side elevation view of a horizontal axis wing turbine, according to the prior art.

FIG. 1 is a side elevation view of a horizontal axis wind turbine 10, according to the prior art. Wind turbine 10 includes a tower 100 supported by and extending from a surface S, such as a ground surface. Supported by tower 100, in turn, is a nacelle 200 extending horizontally. A hub with a spinner 300 is rotatably mounted at a front end of nacelle 200 and is rotatable with respect to nacelle 200 about a rotation axis R. Spinner 300 receives and supports multiple rotor blades 400 that each extend outwardly from spinner 300. Rotor blades 400 catch incident wind W, flowing towards the wind turbine 10 and are caused to rotate. Due to their being supported by spinner 300, rotor blades 400 when rotating cause spinner 300 to rotate about rotation axis R thereby to cause rotational motion that can be converted in a well-known manner into usable electrical or mechanical power. In this sense, rotor blades 400 are each structures adapted to traverse a fluid environment, where the fluid in this embodiment is ambient air. Nacelle 200 may be rotatably mounted to tower 100 such that nacelle 200 can rotate about a substantially vertical axis (not shown) with respect to tower 100, thereby to enable rotor blades 400 to adaptively face the direction from which incident wind W, is approaching wind turbine 10. A nose cone 500 of generally a uniform paraboloidal shape is shown mounted to a front end of spinner 300 to deflect incident wind W, away from spinner 300.

Figure 2:
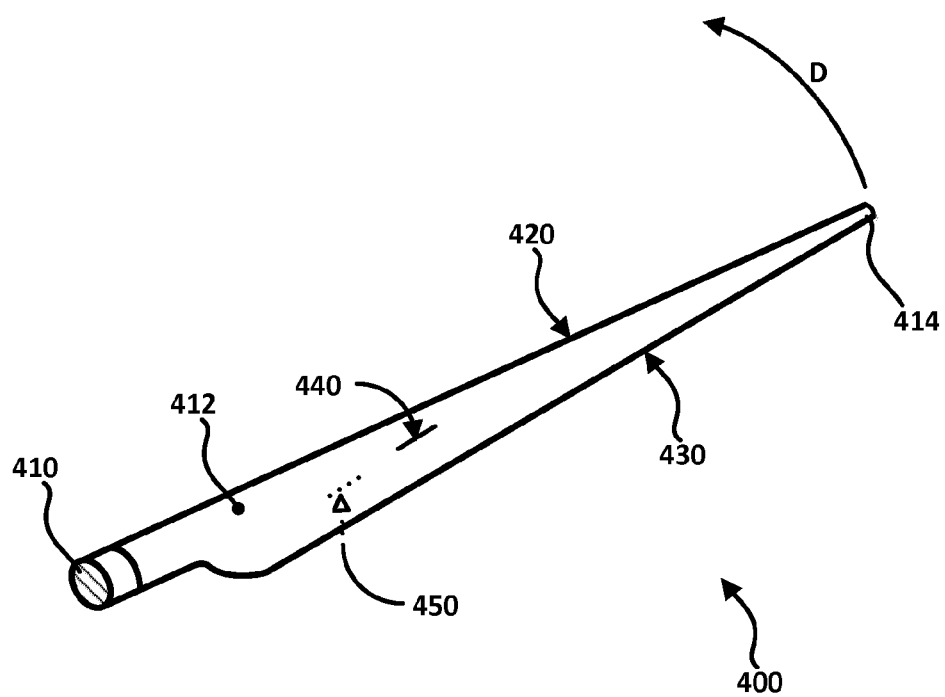
FIG. 2 is a front perspective view of a rotor blades for the turbine of FIG. 1, in isolation, according to the prior art.

FIG. 2 is a front perspective view of one of rotor blades 400 in isolation. Rotor blade 400 includes an elongate body that extends from a root 410 through a main section 412 to terminate at a wingtip 414. Root 410 extends from nacelle 200 when attached thereto or integrated therewith, whereas wingtip 414 is the portion of the elongate body that is distal to nacelle 200. The elongate body has a leading edge 420 and a trailing edge 430, where leading edge 420 leads trailing edge 430 when rotor blade 400 is in motion rotating with nacelle 200 about rotation axis R in the direction D. A suction side 440 of the elongate body is shown in FIG. 2, and a pressure side 450, shown in dotted lines, is opposite the elongate body from suction side 440.

Figure 3:
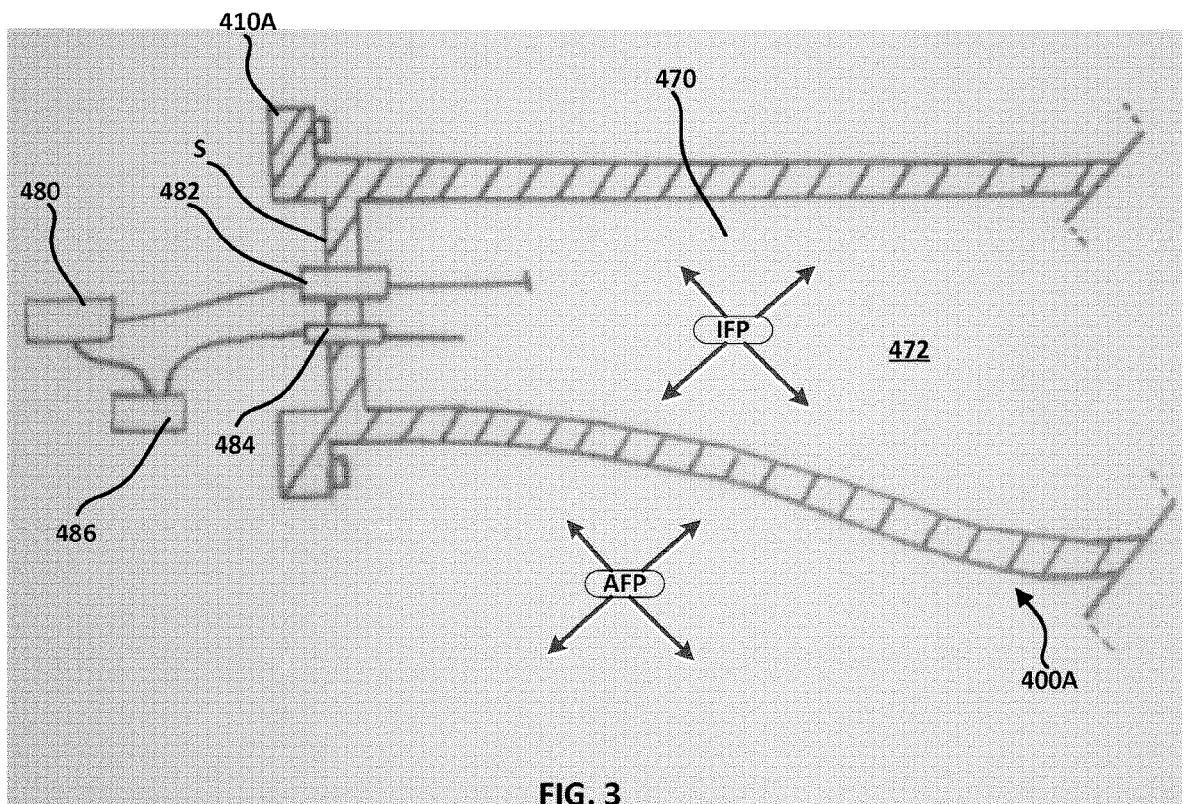
FIG. 3 is a cross-sectional view of a root end of the elongate body of a rotor blade, according to an embodiment of the invention.

FIG. 3 is a cross-sectional view of a root end 410A of the elongate body of a rotor blade 400A, according to an embodiment of the invention. Root 410A is sealed with a seal S around its circumference thus completing the encapsulation of an interior volume 470 within the elongate body. Interior volume 470 contains an interior fluid 472. According to the invention, the interior fluid 472 is present in quantities within the interior volume 470 so as to exert an interior fluid pressure IFP that is different from the ambient fluid pressure AFP that is to be exerted by a fluid environment on the rotor blade 400A during its use. Preferably seal S can be selectively removed and put back into place for the purpose of enabling access to the interior volume 470 for maintenance and the like.

In this embodiment, the interior fluid pressure IFP is less than the ambient fluid pressure AFP, and the interior fluid 472 is primarily nitrogen. Nitrogen is lighter than air and its use as the interior fluid 472 provides an overall weight of rotor blade 400A that is lighter than if interior fluid 472 were to be air. However, in alternative embodiments, interior fluid 472 could comprise air and/or other gases such as one or more noble gases including helium, neon, argon, krypton, xenon and/or other gases that preferably have low chemical reactivity.

Furthermore, in alternative embodiments, the interior fluid 472 could exert an interior fluid pressure IFP that is more than the ambient fluid pressure AFP.

Figure 4:
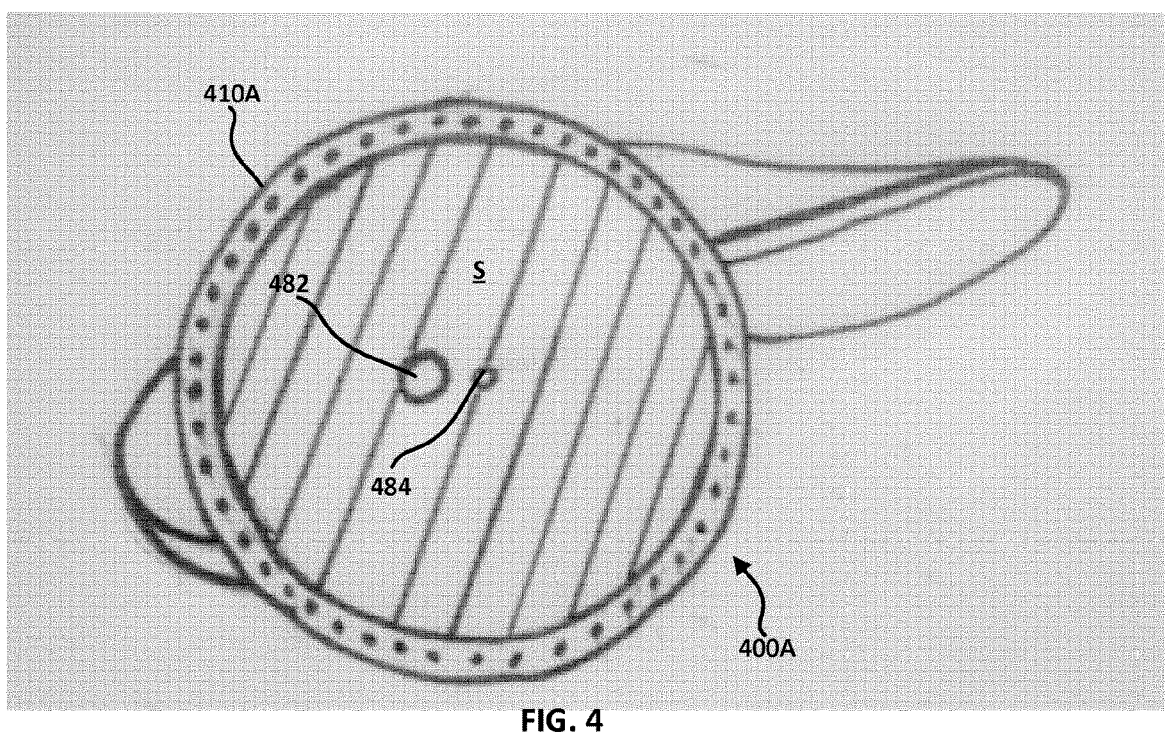
FIG. 4 is an end view of the root end of the rotor blade of FIG. 3.

In the embodiment shown in FIGS. 3 and 4, a hydraulic injector pump 480 is in fluid communication with a valve 482 associated with the elongate body. In this embodiment, the valve 482 extends through seal S and is selectively configurable so as to enable interior fluid to be injected into or drawn from interior volume 470, as well as to selectively prevent neither entry nor egress of interior fluid, as desired. In embodiments involving an interior fluid pressure IFP being less than the ambient fluid pressure AFP, an alternative valve may be a check valve structure that is configured with respect to the interior volume 470 to enable only drawing-out of interior fluid so as to selectively reduce the interior fluid pressure IFP. In embodiments involving an interior fluid pressure IFP being more than the ambient fluid pressure AFP, an alternative valve may be a check valve structure that is configured with respect to the interior volume 470 to enable only injecting-in of interior fluid so as to selectively increase the interior fluid pressure IFP. While only one valve 482 is shown, more than one valve 482 may be employed. For example, a structure according to alternative embodiments may have more than one interior volume encapsulating an interior fluid, and a valve may be provided for each interior volume.

The embodiment shown in FIGS. 3 and 4 further comprises a fluid pressure sensor 484 extending through seal S into the interior volume 470. Fluid pressure sensor 484 is in communication with a processing structure 486 and provides processing structure 486 with electronic or electrical data indicative of the level of the interior fluid pressure IFP of interior fluid 472 within interior volume 470. Processing structure 486 is, in turn, in communication with hydraulic injector pump 480. Processing structure 486 is configured with computer-readable software code stored on a computer readable medium to provide an alert system and to provide logic to enable processing structure 486 to serve as the controller of a pressure regulation system such that, in the event that processing structure 486 receives data indicative of the level of the interior fluid pressure IFP rising above or dropping below a threshold level, processing structure 486 can generate an alert and/or can instruct hydraulic injector pump 480 to inject more interior fluid 472 into interior volume 470 via valve 482, or can trigger valve 482 to release interior fluid thereby to bring the interior fluid pressure IFP to a desired level.

The alert generating system provides early warning to a wind turbine operator as to damage to a rotor blade, since a rapid pressure change is an indication that a crack or hole has developed in the rotor blade. Operations can be rapidly ceased so that maintenance or replacement can be done on demand, rather than necessarily in response to periodic manual inspections that are costly in terms of time offline and personnel involvement.

In this embodiment, the valve 482 and the fluid pressure sensor 484 are positioned at the root end of the elongate body to be located near to the nacelle of a wind turbine that includes the structures as rotor blades extending from its hub. In this embodiment, both the processing structure 486 and the hydraulic injector pump 480 are located within the hub. In the event that the communication between the hydraulic injector pump 480 and the processing structure 486 is wireless and/or the communication between the fluid pressure sensor 484 is wireless, the processing structure 486 can be placed elsewhere, such as within the nacelle. The embodiment shown in FIGS. 3 and 4 is the result of a retrofitting of a known rotor blade. A rotor blade or other structure adapted to traverse a fluid environment exerting an ambient fluid pressure and having an elongate body extending from a root to a wingtip and having at least one interior volume may be retrofitted by sealing the elongate body to encapsulate the at least one interior volume containing an interior fluid, associating a valve with the at least one interior volume; and modifying the interior fluid content via the valve to produce an interior fluid pressure that is different from the ambient fluid pressure.

In this embodiment, the sealing included sealing the elongate body at the root, and the modifying interior fluid content included pumping air out of the at least one interior volume via the valve and pumping nitrogen as into the at least one interior volume via the valve.

In alternative embodiments, retrofitting may include associating more than one valve with the elongate body so as to modify interior fluid content of a number of encapsulated interior volumes of the structure. In embodiments, fluid may be simply pumped into an interior volume via a valve to increase the interior fluid pressure, or fluid may be simply pumped out of the interior volume via a valve to decrease the interior fluid pressure.

In alternative embodiments, a new-build structure similar to those described herein may be formed so as to be sealed and with appropriate valve structure for modifying the interior fluid content.

In embodiments, the interior fluid pressure IFP of the structure may be maintained to be higher than the ambient fluid pressure AFP, such as having an interior fluid pressure of about 1 to about 100 pounds per square inch (PSI). In such embodiments, the structure may be heavier than those structures in which the interior fluid pressure IFP is maintained to be lower than the ambient fluid pressure AFP. However, where the structure is a rotor blade for a wind turbine, momentum of a slightly heavier rotor blade in the face of gusty/erratic wind conditions may be improved.

The beneficial aspects include longer structure life spans, particularly where the structure is a rotor blade for a wind turbine, and lower operating costs for wind farm owners, increased warranty periods for newly built rotor blades and a decreased overall cost to the wind industry.

Although embodiments have been described with reference to the drawings, those of skill in the art will appreciate that variations and modifications may be made without departing from the spirit and scope thereof as defined by the appended claims.

The above-described rotor blade configurations for a horizontal-axis wind turbine can also be applied to one or more rotor blades usable for vertical-axis wind turbines, and both of any scale, or to one or more rotor blades usable in hydroelectric dam turbines, gas turbines, tidal turbines or airborne wind energy turbines or in other kinds of turbines dealing with fluid flow whether of gas or of liquid.

The above-described rotor blade configurations may alternatively be employed in aircraft such as commercial airliners, military jet aircraft, helicopter blades, helicopter wings, civilian airplanes, drones, and other similar aircraft. The invention or inventions described herein may be applied to wind turbines having fewer or more blades than described by way of example in order to increase the operational efficiency of a wind turbine, to decrease maintenance costs, and to increase the scalability and marketability of such wind turbines.

It is observed that commercial airliners, civilian airplanes, drones, helicopter wings would have a winglet of similar size ratio to those of modern commercial airliners, with an architecture that bends back beyond the line of the trailing edge.

A structure as described herein may, as appropriate, contain additional features such as those described in PCT International Patent Application No. PCT/CA2015/050741 to Ryan Church entitled "STRUCTURE WITH RIGID PROJECTIONS ADAPTED TO TRAVERSE A FLUID ENVIRONMENT", and/or those described in PCT International Patent Application No. PCT/CA2015/050740 to Ryan Church entitled "STRUCTURE WITH RIGID WINGLET ADAPTED TO TRAVERSE A FLUID ENVIRONMENT", the contents of each of which are incorporated herein by reference.

Structures such as those described herein may apply equally well, mutatis mutandis, with such mutations as being relevant, including but not limited to, commercial airliners, military jet aircraft, helicopter blades, helicopter wings, civilian airplanes, spacecraft, drones, and other things.

Furthermore, the structures disclosed herein are usable in other fluid environments besides ambient air, such as water environments, oil environments and so forth.

The structure adapted to traverse a fluid environment may be applied to a vertical-axis wind turbine.

The structure adapted to traverse a fluid environment may be applied to a hydroelectric dam turbine.

The structure adapted to traverse a fluid environment may be applied to gas turbines.

The structure adapted to traverse a fluid environment may be applied to tidal turbines.

The structure adapted to traverse a fluid environment may be applied to an airborne wind energy turbine.

The structure adapted to traverse a fluid environment may be applied to a commercial airliner.

The structure adapted to traverse a fluid environment may be applied to a military jet aircraft and to a spacecraft.

The structure adapted to traverse a fluid environment may be applied to a helicopter blade.

The structure adapted to traverse a fluid environment may be applied to helicopter wings.

The structure adapted to traverse a fluid environment may be applied to wings of civilian airplanes.

The structure adapted to traverse a fluid environment may be applied to wings of a drone.

It should be noted that the term 'comprising' does not exclude other elements or steps and the use of articles "a" or "an" does not exclude a plurality. Also, elements described in association with different embodiments may be com-

What is claimed is:

1. A method of retrofitting a structure adapted to traverse a fluid environment exerting an ambient fluid pressure, the structure comprising an elongate body extending from a root to a wingtip and having at least one interior volume, the method comprising:
   sealing the elongate body to encapsulate the at least one interior volume containing an interior fluid;
   associating a pressure sensor for sensing a level of interior fluid pressure with the at least one interior volume; and
   generating an alert with an alert system in communication with the pressure sensor, in response to the pressure sensor detecting the level of interior fluid pressure below, or above, a threshold level indicative of structural damage to the elongate body.

2. The method of claim 1, wherein the sealing the elongate body comprises sealing the elongate body at the root with a releasable and reusable seal.

3. The method of claim 1, further comprising:
   associating at least one valve with the at least one interior volume; and
   modifying interior fluid content via the at least one valve to produce the level of interior fluid pressure below, or above, the threshold level indicative of structural damage to the elongate body.

4. The method of claim 3, wherein the modifying interior fluid content via the at least one valve comprises:
   pumping fluid into the at least one interior volume via the at least one valve.

5. The method of claim 3, wherein the modifying interior fluid content via the at least one valve comprises:
   pumping fluid out of the at least one interior volume via the at least one valve; and
   pumping a noble gas into the at least one interior volume via the at least one valve.

6. The method of claim 4, wherein the fluid is nitrogen.

7. A turbine comprising:
   a hub;
   a plurality of structures extending from the hub and adapted to traverse a fluid environment exerting an ambient fluid pressure, each of the plurality of structures comprising:
   (i) an elongate body extending from a root to a wingtip and encapsulating at least one interior volume containing an interior fluid exerting an interior fluid pressure that is different from the ambient fluid pressure; and
   (ii) a pressure sensor associated with the elongate body for sensing a level of interior fluid pressure; and
   an alert system in communication with the pressure sensor and configured to generate an alert in response to the pressure sensor detecting the level of interior fluid pressure below, or above, a threshold level indicative of structural damage to the elongate body.

8. The turbine of claim 7, further comprising:
   at least one valve, connected to each of the elongate bodies, configurable to enable fluid to be injected into or drawn from the at least one interior volume; and
   at least one fluid pump associated with the hub and in fluid communication with the at least one valve;
   wherein the alert system is further configured to, in response to the pressure sensor detecting the level of interior fluid pressure below, or above, a desired level, actuate the at least one fluid pump to increase, or decrease, respectively, the interior fluid pressure back to the desired pressure.

9. The turbine of claim 7, wherein the interior volume is encapsulated within the elongate body by a releasable seal.

10. The turbine of claim 9, wherein the releasable seal is located at the root.

11. The turbine of claim 7, wherein the interior fluid is a gas with low chemical reactivity.

12. The turbine of claim 7, wherein the interior fluid pressure is maintained at 1 to 100 pounds per square inch (psi).

13. The turbine of claim 7, wherein the alert system is configured to cease operation of the turbine in response to the pressure sensor detecting the level of interior fluid pressure below, or above, a threshold level indicative of structural damage.

14. The turbine of claim 7, wherein the alert system is within the hub.

15. The turbine of claim 7, wherein the alert system wirelessly communicates with the pressure sensor.

16. The turbine of claim 7, wherein the alert system is associated with the hub or a nacelle.

17. A method of operating an alert system comprising:
   receiving an indication of a level of interior fluid pressure on an internal fluid below or above a threshold level indicative of structural damage to an elongate body from a pressure sensor, the elongate body extending from a root to a wingtip and encapsulating an interior volume containing the interior fluid,
   transmitting an alert indicative of the interior fluid pressure on the internal fluid below or above the threshold level indicative of structural damage to the elongate body, and
   transmitting a command to cease operation of a turbine associated with the elongate body.

18. The method of operating the alert system of claim 17, further comprising:
   actuating at least one fluid pump in fluid communication with at least one valve connected to the elongate body to pump additional fluid into the interior volume increasing a weight of the elongate body to an erratic wind resistance weight while maintaining a desired interior fluid pressure.

19. The method of operating the alert system of claim 17, further comprising:
   actuating at least one fluid pump in fluid communication with at least one valve connected to the elongate body to remove interior fluid decreasing a weight of the elongate body while maintaining a desired interior fluid pressure.

20. The method of operating the alert system of claim 17, wherein the alert system is associated with a hub or a nacelle connected to the elongate body.

* * * * *